United States Patent [19]

Holloway et al.

[11] Patent Number: 5,244,923

[45] Date of Patent: Sep. 14, 1993

[54] USE OF 2-(PHENOXYPROPANOLAMINO) ETHOXPHENOXY-ACETIC ACID AND ITS DERIVATIVES TO INHIBIT GASTROINTESTINAL MOTILITY

[75] Inventors: Brian R. Holloway; James W. Growcott, both of Cheshire, England

[73] Assignee: Imperial Chemical Industries PLC, London, England

[21] Appl. No.: 736,952

[22] Filed: Jul. 30, 1991

[30] Foreign Application Priority Data

Jul. 30, 1990 [GB] United Kingdom ............... 9016655

[51] Int. Cl.$^5$ ........................................... A61K 31/165
[52] U.S. Cl. ........................................... 514/620
[58] Field of Search ........................... 514/567, 620

[56] References Cited

U.S. PATENT DOCUMENTS

| | | | |
|---|---|---|---|
| 4,772,631 | 9/1988 | Holloway | 514/539 |
| 4,927,836 | 5/1990 | Holloway | 514/620 |
| 4,977,148 | 12/1990 | Holloway | 514/183 |
| 5,002,946 | 3/1991 | Manara et al. | 514/230.8 |

OTHER PUBLICATIONS

Manara et al., Trends Pharmacol. Sci., pp. 229–230 (1990).

*Primary Examiner*—Frederick E. Waddell
*Assistant Examiner*—Kimberly R. Jordan
*Attorney, Agent, or Firm*—Cushman, Darby & Cushman

[57] ABSTRACT

The use of a compound of the formula (I):

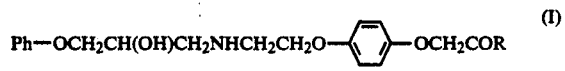

wherein R is hydroxy or 2-methoxyethylamino or a pharmaceutically acceptable salt thereof, in stimulating the 'atypical' β-adrenoceptors in the gastrointestinal tract and thereby inhibiting gastrointestinal motility. These compounds may be used for treating medical conditions wherein inhibition of gastrointestinal motility is thought to be of value, such as in the treatment of inflammatory bowel disease, irritable bowel syndrome (IBS), non specific diarrhoea and dumping syndrome.

7 Claims, No Drawings

USE OF 2-(PHENOXYPROPANOLAMINO) ETHOXPHENOXY-ACETIC ACID AND ITS DERIVATIVES TO INHIBIT GASTROINTESTINAL MOTILITY

The present invention relates to 2-(phenoxypropanolamino)ethoxyphenoxyacetic acid derivatives and in particular to the use of such derivatives in the therapeutic treatment of animals including humans. These derivatives stimulate the "atypical" $\beta$-adrenoceptors in the gastrointestinal tract and therefore inhibit gastrointestinal motility. They may be of use in combatting medical conditions wherein stimulation of "atypical" $\beta$-adrenoceptors in the gastrointestinal tract is thought to be beneficial, such as in combating medical conditions wherein inhibition of gastrointestinal motility is thought to be of value. Thus they may be of use for example in the treatment of inflammatory bowel disease (IBD) (such as Crohn's disease and ulcerative colitis), irritable bowel syndrome (IBS), non specific diarrhoea and dumping syndrome.

Accordingly the present invention provides a method of stimulating the "atypical" $\beta$-adrenoceptors in the gastrointestinal tract which comprises administering, to an animal in need thereof, a therapeutically effective amount of a compound of formula (I):

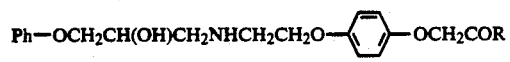
(I)

Ph—OCH$_2$CH(OH)CH$_2$NHCH$_2$CH$_2$O—⟨ ⟩—OCH$_2$COR wherein R is hydroxy or 2-methoxyethylamino or a pharmaceutically acceptable salt thereof.

In one aspect the present invention provides a method of inhibiting gastrointestinal motility which comprises administering to an animal in need thereof, a therapeutically effective amount of a compound of formula (I) or a pharmaceutically acceptable salt thereof.

In yet another aspect the present invention provides the use of a compound of formula (I) or a pharmaceutically acceptable salt thereof for the manufacture of a medicament for stimulating the "atypical" $\beta$-adrenoceptors in the gastrointestinal tract.

In another aspect the present invention provides the use of a compound of formula (I) or a pharmaceutically acceptable salt thereof for the manufacture of a medicament for inhibiting gastrointestinal motility.

In a further aspect the invention provides a method of treating IBD, which comprises administering, to an animal in need thereof, a therapeutically effective amount of a compound of the formula (I) or a pharmaceutically acceptable salt thereof.

In a further aspect the invention provides a method of treating IBS, which comprises administering, to an animal in need thereof, a therapeutically effective amount of a compound of the formula (I) or a pharmaceutically acceptable salt thereof.

In a further aspect the invention provides a method of treating non specific diarrhoea, which comprises administering, to an animal in need thereof, a therapeutically effective amount of a compound of the formula (I) or a pharmaceutically acceptable salt thereof.

In a further aspect the invention provides a method of treating gastric emptying in dumping syndrome, which comprises administering to an animal in need thereof, a therapeutically effective amount of a compound of formula (I), or a pharmaceutically acceptable salt thereof.

In a further aspect the present invention provides the use of a compound of formula (I) or a pharmaceutically acceptable salt thereof for the manufacture of a medicament for treating IBD.

In a further aspect the present invention provides the use of a compound of the formula (I) or a pharmaceutically acceptable salt thereof for the manufacture of a medicament for treating IBS.

In a further aspect the present invention provides the use of a compound of the formula (I) or a pharmaceutically acceptable salt thereof for the manufacture of a medicament for treating non specific diarrhoea.

In yet a further aspect the present invention provides the use of a compound of the formual (I) or a pharmaceutically acceptable salt thereof for the manufacture of a medicament for treating gastric emptying in dumping syndrome.

Preferably in the compound of formula (I) R is 2-methoxyethylamino.

The compounds of formula (I) contain an asymmetric carbon atom and can exist as an optically active enantiomer (R or S according to the Cahn-Ingold-Prelog convention) or as an optically inactive racemate. The compounds for use in the present invention contain at least some of the laevorotatory optically active form (−) which corresponds to the (S) absolute configuration. Conveniently the compounds for use in the present invention are provided as the racemate, but preferably are provided as the laevorotatory optically active form (−).

The compounds of formula I are basic and may be isolated and used either in the form of a free or of a pharmaceutically acceptable acid-addition salt thereof. In addition, the compound of the formula (I) wherein R is hydroxy is amphoteric and may be isolated and used in the zwitterionic form, or as a pharmaceutically acceptable acid-addition salt, or as a salt with a base affording a pharmaceutically acceptable cation.

Particular examples of pharmaceutically acceptable acid-addition salts include, for example, salts with inorganic acids such as hydrohalides (especially hydrochlorides or hydrobromides), sulphates and phosphates, and salts with organic acids such as the free acid form of sulphonated polystyrene.

Particular examples of salts with bases affording a pharmaceutically acceptable cation include, for example, alkali metal and alkaline earth metal salts, such as sodium, potassium, calcium and magnesium salts, and ammonium salts and salts with suitable organic bases, such as triethanolamine.

A preferred compound for use in the methods of the present invention is:

(S)-4-[2-(2-hydroxy-3-phenoxypropylamino)ethoxy]-N-(2-methoxyethyl)phenoxyacetamide hydrochloride.

The compound of the formula (I) and pharmaceutically acceptable salts thereof wherein R is hydroxy are known from, and/or can be prepared by, the methods of European Patent Application Publication No 210849. The compound of the formula (I) and pharmaceutically acceptable salts wherein R is 2-methoxyethylamino are known from, and/or can be prepared by, the methods of European Patent Application Publication No 254532.

The compounds of the formula (I) and their pharmaceutically acceptable salts are known as thermogenic agents, that is they stimulate thermogenesis in warm-blooded animals and are of use, for example, in the treatment of obesity and related conditions, such as obesity of mature onset diabetes. These compounds may also be of value in the modification of carcass composition, for example, by increased catabolism of fat in meat producing animals, such as cattle, pigs, sheep, goats and/or rabbits.

We have now discovered that the compounds of the formula (I) and their pharmaceutically acceptable salts inhibit gastrointestinal motility and are therefore of use in treating disease conditions such as IBD, IBS, non specific diarrhoea and gastric emptying in dumping syndrome.

In order to use the compounds of the formula (I) and pharmaceutically acceptable salts thereof to inhibit gastrointestinal motility, they are normally formulated in accordance with standard pharmaceutical practice as a pharmaceutical composition.

The pharmaceutical compositions of this invention may be administered in standard manner for example by oral, rectal or parenteral administration. For these purposes they may be formulated by means known in the art into the form of for example, tablets, capsules, pills, powders, suppositories, aqueous or oily solutions or suspensions, emulsions and sterile injectable aqueous or oily solutions or suspensions.

In general compositions for oral administration are preferred.

The compositions may be obtained using standard excipients and procedures known in the art. A unit dose form such as a tablet or capsule will usually contain for example 0.1-250 mg of active ingredient. The compositions may also contain other active ingredients known for use in the treatment of IBS or IBD and related conditions, for example in anti diarrhoea formulations:
morphine
bulking agent
and/or cholestyramine
and in formulations specifically for IBD:
steroids
and/or salazopyrine When used to inhibit gastrointestinal motility in warm-blooded animals including man, a compound of the formula (I) or a pharmaceutically acceptable salt will be administered so that a dose in the general range 0.002-20 mg/kg and preferably in the range 0.02-10 mg/kg, is administered daily, given in a single dose or divided doses as necessary. However, it will be appreciated by those skilled in the art that the dosage will necessarily be varied as appropriate, depending on the severity of the condition under treatment and on the age and sex of the patient and according to known medical principles.

The effects of a representative compound for use in a method according to this invention are described in the following example:

EXAMPLE 1

Lengths of guinea-pig ileum (2 cm) removed 10 cm from the ileo-caecal junction were set up under a resting tension of 500 mg in a 5 ml organ bath containing Krebs solution [NaCl (118 mM), $CaCl_2$ (2.52 mM), KCl (4.6 mM), $NaHCO_3$ (25 mM), $KH_2PO_4$ (1 mM), $MgSO_4$ (1.2 mM), glucose (11.7 mM) and ascorbic acid (0.11 mM)], cocaine (30 $\mu$M), corticosterone (30 $\mu$M), phentolamine (3 $\mu$M), (+)propranolol (5 $\mu$M) and atropine (1 $\mu$M) at 37° C.; 95% $O_2$/5% $CO_2$ was bubbled through continuously to maintain a pH of 7.4.

The concentrations of atropine and phentolamine are at least 100 times their equilibrium dissociation constants for muscarinic receptors and alpha adrenoceptors respectively [Clague, R U et al., (1985) Br. J. Pharmacol. 64, 293-300; Kenakin, T P (1987) In Pharmacological Analysis of Drug-Receptor Interaction, pp. 1-30. New York: Raven Press].

The inhibitory (relaxant) activity of the test compound was determined by measuring the reduction in the contractile response elicited by a submaximal concentration of histamine (0.5 $\mu$M). Thus, histamine was added to the tissue and following contraction, washed out. The tissue was then allowed to recover for 5 min with 5 further wash-outs before adding histamine again. This procedure was repeated until the tissue gave stable responses to histamine (usually after 4-5 doses) and the final stable response was set at 100%, all subsequent responses being expressed as a percentage relaxation. Increasing concentrations of the test compound were added to the tissue 2 min before addition of histamine and were retained in the organ bath during the response to histamine.

The "atypical" $\beta$ adrenoceptor agonist effect was calculated from $EC_{30}$ values (the concentration of agonist producing a relaxation equivalent to 30% histamine inhibition).

| Test compound | $EC_{30}$ ($\mu$M) |
|---|---|
| (S)-4-[2-(2-hydroxy-3-phenoxypropylamino)-ethoxy]-N-(2-methoxyethyl)phenoxyacetamide hydrochloride | 0.94 ± 0.26 |

We claim:

1. A method of stimulating the 'atypical' $\beta$-adrenoceptors in the gastrointestinal tract which comprises administering to a patient in need thereof an effective amount of a compound of the formula (I):

wherein R is 2-methoxyethylamino or a pharmaceutically acceptable salt thereof.

2. A method of inhibiting gastrointestinal motility which comprises administering to a patient in need thereof an effective amount of a compound of the formula (I):

wherein R is 2-methoxyethylamino or a pharmaceutically acceptable salt thereof.

3. A method of treating inflammatory bowel disease which comprises administering to a patient in need thereof an effective amount of a compound of the formula (I):

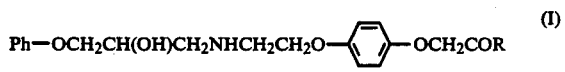

wherein R is 2-methoxyethylamino or a pharmaceutically acceptable salt thereof.

4. A method according to any one of claims 1 to 3 wherein the compound of the formula (I) or pharmaceutically acceptable salt thereof is in the laevorotatory optically active form (−).

5. A method according to claim 4 wherein the compound of the formula (I) is (S)-4-[2-(2-hydroxy-3-phenoxypropylamino)ethoxy]-N-(2-methoxyethyl)-phenoxyacetamide hydrochloride.

6. A method according to claims 1 to 3 wherein the medicament is suitable for oral administration.

7. A method according to claim 4 wherein the medicament is suitable for oral administration.

* * * * *